United States Patent [19]

Sage, Jr.

[11] Patent Number: 4,600,302
[45] Date of Patent: Jul. 15, 1986

[54] FLOW CYTOMETRY APPARATUS WITH UNIFORM INCOHERENT LIGHT EXCITATION

[75] Inventor: Burton H. Sage, Jr., Raleigh, N.C.

[73] Assignee: Becton, Dickinson and Company, Franklin Lakes, N.J.

[21] Appl. No.: 593,470

[22] Filed: Mar. 26, 1984

[51] Int. Cl.⁴ ...................... G01N 33/48; G01N 21/64
[52] U.S. Cl. ................................... 356/39; 250/461.2; 356/317
[58] Field of Search ...................... 356/39, 72, 73, 317, 356/318; 362/32; 250/461.2

[56] References Cited

U.S. PATENT DOCUMENTS

| | | | |
|---|---|---|---|
| 3,792,248 | 2/1974 | Dietz | 362/32 |
| 4,348,107 | 9/1982 | Leif | 356/72 |
| 4,451,149 | 5/1984 | Noeller | 250/461.2 X |
| 4,498,766 | 2/1985 | Unterleitner | 356/73 |

FOREIGN PATENT DOCUMENTS 2427182 12/1975 Fed. Rep. of Germany ........ 362/32

*Primary Examiner*—Michael R. Lusignan
*Attorney, Agent, or Firm*—Richard J. Rodrick

[57] ABSTRACT

A flow cytometry apparatus for determining one or more characteristics of particles or the like flowing in a liquid stream includes a nozzle for generating a liquid flow stream for moving particles therethrough substantially one at a time. An arc lamp provides a beam of incoherent light to illuminate the particles moving in the flow stream. A prism in the light beam modifies non-uniform incoherent light, as provided by said arc lamp, to a more uniform beam of illumination which is directed to the flowing particles. A detector is included for detecting light with respect to each moving particle and for associating the detected light with one or more characteristics of the particles.

16 Claims, 3 Drawing Figures

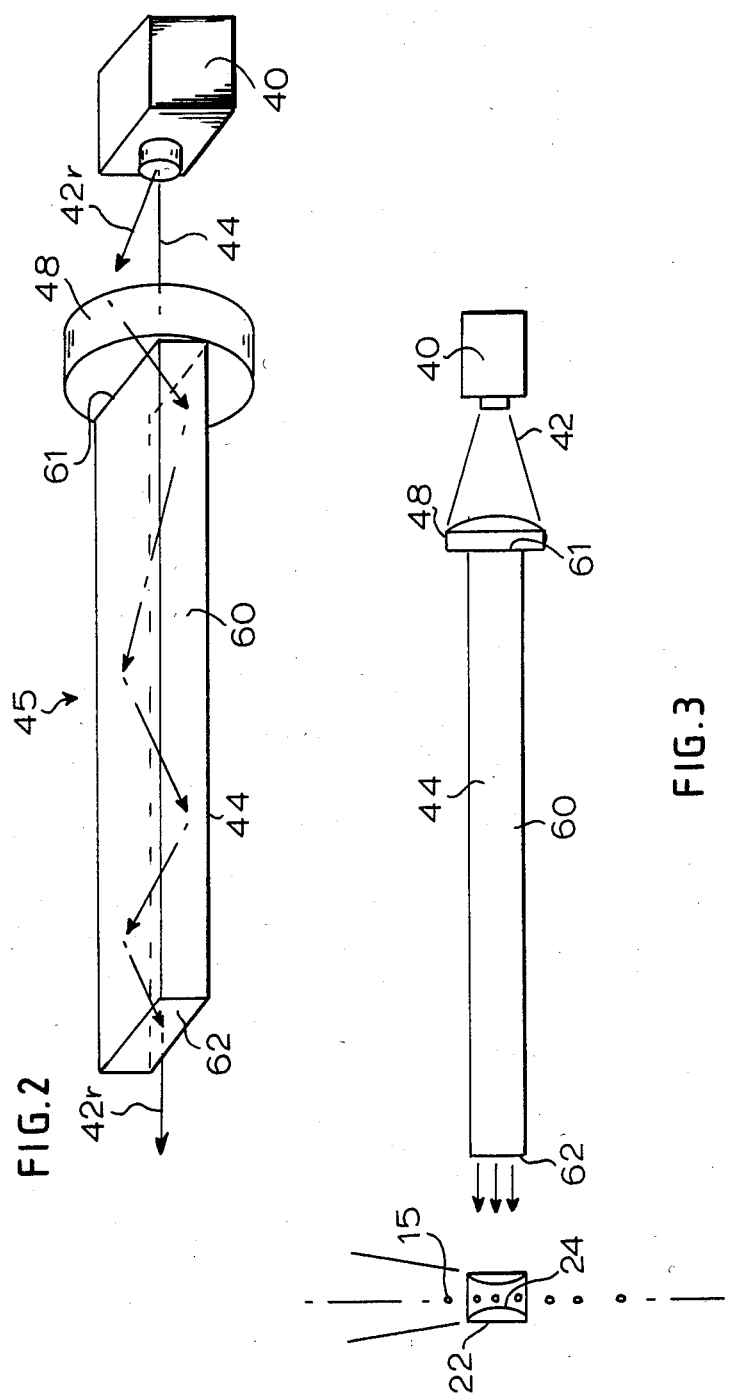

FLOW CYTOMETRY APPARATUS WITH UNIFORM INCOHERENT LIGHT EXCITATION

BACKGROUND OF THE INVENTION

1. Field of the Invention

The present invention relates to a flow cytometry apparatus, and more particularly, concerns a flow cytometry apparatus for determining characteristics of cells or the like, which includes improved optics for obtaining uniform incoherent light excitation of the sample stream.

2. Description of the Prior Art

Flow cytometry apparatuses rely upon the flow of cells or other particles in a liquid flow stream in order to determine one or more characteristics of the cells under investigation. For instance, a liquid sample containing cells is directed through the flow cytometry apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light has served as a function of cell shape, index of refraction, opacity, roughness and the like. Further, fluorescence emitted by labeled cells which have been excited as a result of passing through the excitation energy of the incident light beam is detectable for identification of specifically labeled cells. Not only is cell analysis performed on the flow cytometry apparatuses, but sorting of cells may also be achieved. Lasers have been used as the source of the incident beam of illumination in flow cytometry apparatuses, as well as sources of incoherent or non-collimated light, such as mercury or xenon arc lamps. Such apparatuses have been described in copending patent applications, Ser. No. 276,738, filed on June 24, 1981, in the U.S. Patent and Trademark Office and Ser. No. 482,346, filed in the U.S. Patent and Trademark Office on Apr. 5, 1983, both applications having a common assignee herewith, and also in U.S. Pat. No. 4,348,107. One flow cytometry apparatus known and sold as the FACS TM Analyzer, FACS Systems, Becton, Dickinson and Company, Sunnyvale, Calif., relies upon a mercury arc lamp as the excitation source of incoherent light for illuminating the stream of particles or cells flowing therethrough.

Excitation energy from a mercury or xenon arc lamp is typically bright and spectrally rich. However, as employed in a flow cytometry apparatus, the arc lamp may exhibit two undesirable characteristics. First, the brightness of the arc lamp may not be uniform over the used area of the source of the light. Hence, fluorescently labeled particles, flowing through the flow cytometry apparatus, at which such light is directed, may not be excited uniformly, and the resulting fluorescence emitted by these particles may not be uniform even though the particles themselves may be uniform in their ability to fluoresce. Second, the position of the arc itself, within the light source, may not be stable. As a result, additional fluctuations in the excitation intensity could be produced.

At the present time, there are two alternate techniques, known to those skilled in this art, to rectify the aforementioned undesirable traits associated with the ability of an arc lamp to produce uniform arc images in a flow cytometry apparatus. One technique has been to employ standard Kohler illumination techniques. When using these Kohler techniques, the image of the arc lamp is imaged into the pupil of the excitation objective lens. While this approach may produce uniform time-independent excitation, such excitation is typically spread over the entire field of view of the objective lens resulting in low excitation energy at the moving particle stream within the flow cytometry apparatus. A second technique utilized in this field involves the magnification of the arc image by a large factor followed by directing the enlarged image onto a small slit. Light passing through the slit is then imaged onto the flowing stream of particles by an objective lens. It has been found, however, that most of the light is lost before it reaches the particle flowing stream principally because the light does not pass effectively through the slit.

Accordingly, improvements are still being sought for flow cytometry apparatuses which rely upon an incoherent light source, such as mercury or xenon arc lamps, for producing light to illuminate the particles flowing in the liquid stream. Improvements are needed particularly in providing uniform light energy to the flowing particles so that uniform excitation thereof may be achieved especially when fluorescently labeled particles are being analyzed. It is to such improvement that the present invention is directed.

SUMMARY OF THE INVENTION

The flow cytometry apparatus of the present invention for determining one or more characteristics of particles or the like flowing in a liquid stream comprises means for moving particles, substantially one at a time, in a liquid flow stream. Means provides a spectrally rich beam of originally nonuniform light to illuminate the particles moving in the stream. Means in the light beam modifies the non-uniform light, as provided by the light means, to a more uniform beam of illumination which is directed to the flowing particles. Means for detecting light with respect to each moving particle is included, which also associates the detected light with one or more characteristics of the particles.

In a preferred embodiment of the present invention, an arc lamp provides the light energy, as a beam of incoherent light, to illuminate the particles or cells moving the flow stream. The means to modify the light beam to render it more uniform is preferably an elongate, solid, light transmissive prism having its longitudinal axis aligned substantially along the light beam between the source and the flow stream. Such prism, preferably rectangular in cross-section, includes internally reflective side surfaces and light transmissive end surfaces. Non-uniform light from the arc lamp, directed into the prism through one of its end surfaces, is then modified therein due to the internal reflections, whereupon light exits the prism through the opposite end surface in uniform fashion as it is directed toward the flowing particles or cells in the liquid stream. A lens may be employed adjacent to the one end surface of the prism for focusing light from the arc lamp into the prism for more efficient collection of the light energy.

In accordance with the principles of the present invention, both of the aforementioned undesirable characteristics associated with excitation light from an arc lamp are obviated and overcome. Employment of the preferably elongate light transmissive prism, in lieu of the above-described known techniques of rectifying the arc lamp infirmities, is straightforward and readily adaptable to flow cytometry apparatuses using arc lamps for light energy. Once the light from the arc lamp is inside the prism, its natural divergence causes the light to be reflected, by the above-described internal reflections, at the internal walls of the prism. As a result of these reflections, the point of exit of the light from the prism is totally uncorrelated with the point of entry of light into the prism. Accordingly, the exit end of the prism will be uniformly illuminated by the light, and therefore may be used as a uniform excitation source particularly when fluorescently labeled cells or particles are being analyzed. Employment of the prism as part of the arc lamp excitation system in a flow cytometry apparatus thus efficiently converts a small nonuniform arc image into a slightly larger, very uniform image suitable for uniform excitation of particles flowing in the sample stream. Moreover, the prism reduces the effect of arc wander on excitation intensity. Is is appreciated that the preferably elongate prism is analogous to an optical tunnel for producing the above-described internal reflections ultimately resulting in light uniformly directed from the exit end thereof.

BRIEF DESCRIPTION OF THE DRAWINGS

FIG. 2 is an enlarged perspective view of the preferred rectangular prism of the present invention illustrating the path of a single, isolated light ray therethrough; and FIG. 3 is a side elevational view of the light path of the present invention from light source to liquid flow stream illustrating the function of the prism of the present invention.

DETAILED DESCRIPTION

Figure 1:
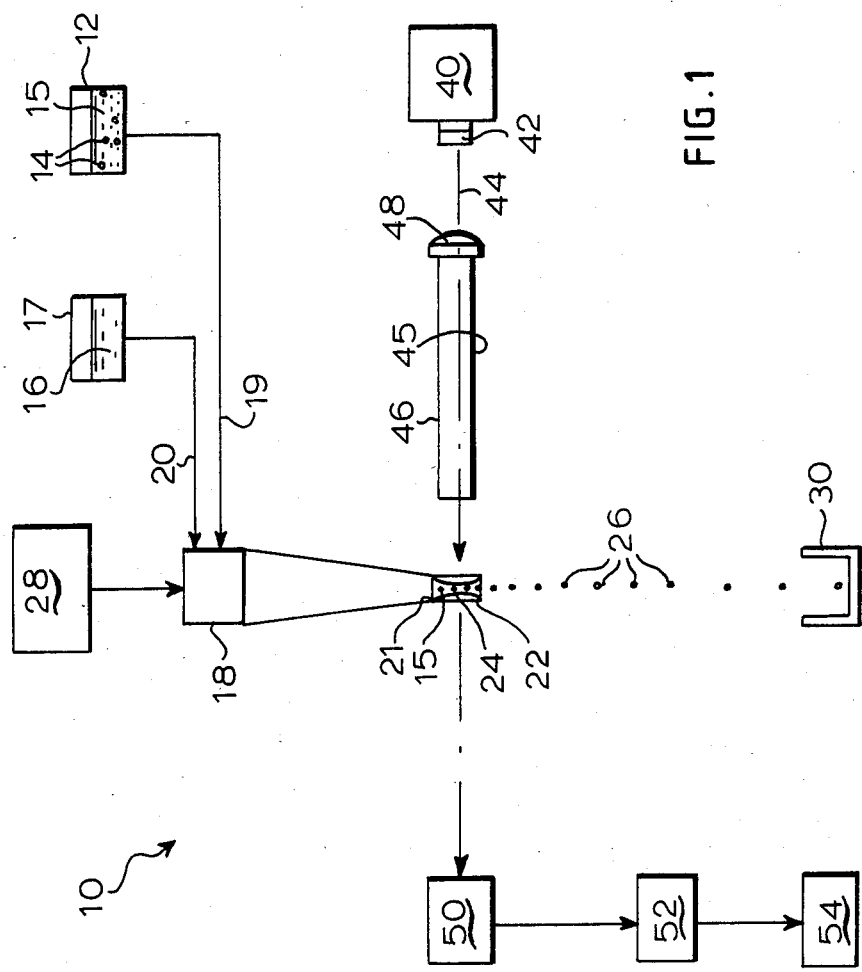
FIG. 1 is a schematic illustration of the major functional elements of the improved flow cytometry apparatus of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Turning first to FIG. 1, there is illustrated a schematic representation of the preferred apparatus 10 embodying flow cytometry principles, and more specifically, utilizing a sheath fluid, in conjunction with a particle stream, in a hydrodynamically focused fluid flow system. It is understood that the present invention is useful in a variety of circumstances related to the determination of one or more characteristics of particles or cells flowing in a moving stream. Accordingly, the present invention is useful, for example, in measuring light scatter, particle volume, fluorescence or any other optical parameters for the identification, classification or quantification of particles in a sample medium.

Apparatus 10 includes a storage container 12 for holding liquid 14 containing particles 15 in suspension which are to be detected or analyzed in accordance with the present invention. A particle free sheath liquid 16 is stored in container 17. Both of the aforementioned containers may be appropriately pressurized by means of a gas pressure source or the like (not shown). Liquids 14 and 16 are supplied to a nozzle assembly 18 through conduits 19 and 20, respectively. A bi-component, coaxial stream of particles 15 is formed within nozzle assembly 18, in known fashion, utilizing liquids 14 and 16. A more detailed explanation of the structure and operation of such a nozzle assembly and the formation of a bi-component coaxial stream of particles is found in the two commonly assigned patent application described above. For purposes of the present description, a continuous coaxial liquid flow stream of particles exits the end 21 of nozzle assembly 18 and is directed preferably, although not necessarily, to a liquid flow chamber 22. This flow chamber is typically transparent, and optically clear, and has an orifice 24 through which particles 15 flow substantially one at a time. The details of liquid flow chamber 22 are also found in the two co-pending patent applications mentioned above. When the coaxial stream of particles and sheath liquid flows through flow chamber 22, the stream containing the particles is normally continuous. Although not necessary for the present invention, it may be desirable to form discrete droplets 26 containing particles of interest after the stream passes through flow chamber 22. To this end, droplets 26, some of which may contain particles 15, may be formed from the continuously flowing liquid stream preferably by vibration of nozzle assembly 18. To accomplish this feature, a transducer and driver amplifier 28 may be provided to vibrate the nozzle assembly in an axial direction. Such vibration modulates the flowing liquid stream to disrupt its continuous flow and cause discrete droplets to be formed. These droplets may then be collected in one or more containers 30.

As is known in flow cytometry apparatuses, a source of light, for excitation or scatter purposes, is provided to illuminate the particles flowing in the liquid stream. In the invention at hand, the source of illumination is an incoherent or non-collimated light source such as a mercury or xenon arc lamp 40. A spectrally rich light beam 42 from the arc lamp is directed toward the particles flowing in the liquid stream so as to intercept the particles at a substantially right angle. Thus, and as seen in FIG. 1, light beam 42 from arc lamp 40 is aligned along axis 44 extending substantially orthogonally to the flowing liquid stream of particles 15 and intersecting flow chamber 22 through orifice 24. Positioned between arc lamp 40 and flow chamber 22 (enclosing the liquid stream of particles 15) is a prism assembly 45 comprising two components, namely, an elongate, solid, light transmissive prism 46 and a lens element 48. It can be seen in FIG. 1 that lens element 48 is preferably in contact with prism 46 and faces arc lamp 40. Light beam 42 travels first into lens 48 and then through prism 46 before striking particles 15 flowing through flow chamber 22, the details of which will be described more completely hereinafter. It may be desirable to include another focusing lens between prism 46 and flow chamber 22 to focus the light which strikes the particles. Light exiting the prism illuminates the flow chamber so that particles passing therethrough intersect a field of light.

Light scattered, emitted or otherwise associated with the particles passing through the illuminated area of the flow chamber is then detected by light detector 50. This light detector may be a well-known photomultiplier device which converts light signals to electrical pulses so that information with respect to the detected light may be electrically analyzed. Thus, detector 50 may detect fluorescence emitted by the particles passing through the area of illumination, or light scattered by the particles passing through the illuminated area. More than one detector may be included in the present invention in various combinations. The electrical pulse associated with detected light may be fed to the electronics 52 of the flow cytometry apparatus whereupon information relating thereto may be seen on a display 54, stored in a computer (not shown) or fed back into the apparatus for further analysis.

Referring now to FIG. 2, preferred prism assembly 45 is illustrated along with arc lamp 40. To graphically illustrate the function of prism assembly 45, the path of a single, isolated light ray 42r (as part of light beam 42) is depicted. It is understood, however, that light beam 42 consists of many different rays of light of different wavelengths, intensities and directions. This multiplicity of light characteristics is inherent in the nature of light from a source such as a mercury or xenon arc lamp 40. As mentioned above, light from the arc lamp is not only bright and spectrally rich, but the nature of light emanating from the source is normally non-uniform and the position of the arc is unstable and tends to wander. Accordingly, a single light ray 42r may exit arc lamp 40 in the direction as schematically illustrated in FIG. 2.

Before describing the course of light ray 42r through prism assembly 45, the details and structure of the prism assembly will now be described. Prism 46 is preferably an elongate, solid, light transmissive prism, having a rectangular cross-section. It is understood, however, that the present invention does not restrict the prism to a rectangular cross-section, and that other shapes may be utilized, where appropriate and feasible. Prism 46 has the outside of its four side surfaces 60 preferably coated with a material to protect those surfaces and prevent the degradation of normal total internal reflection. As a practical effect, the coating on the outer side surfaces, while not necessary, aids in preventing dirt, dust, grease, fingerprints, and the like, from adhering to the prism.

A first end surface 61, also referred to as the entry end, and a second end surface 62, also referred to as an exit end of prism 46, is transmissive to light. Preferably, surfaces 61 and 62 are treated with an anti-reflectance agent to improve the efficiency of light transmission therethrough. The elongate nature of prism 46 gives it the appearance of a slender rod inasmuch as the cross section of the prism is substantially constant along its longitudinal axis. The length of the prism and the aspect ratio of its rectangular cross-section may be emperically determined or specifically designed by those skilled in the art for emloyment in the specific type of flow cytometry apparatus at hand. With respect to the cross-sectional width of the prism, it is preferred that such width be greater than the width of incident beam 42 of incoherent light which enters entry end 61 of the prism. This preferred width of the prism facilitates the solution of the arc wander situation so that substantially all light from the arc lamp can be directed into the prism.

To further facilitate the direction of light into the prism, lens element 48 is provided. This lens element, when included in the present invention, is positioned between arc lamp 40 and prism 46 so that the arc appears as though it is infinitely distant. This insures that the divergence of the light exiting surface 62 is minimal, providing for optimal excitation intensity in particle stream 15. If practicable, prism 46 and lens 48 may be integrally formed as a unitary structure from the same light transmissive material. Preferably, the prism and the lens, whether provided separately or as an integral unit, are made of glass, and most desirably, solid quartz.

As seen in FIG. 2, taken in conjunction with FIG. 1, prism 46 has its longitudinal axis aligned substantially along axis 44 of light beam 42 and is positioned between arc lamp 40 and particles 15 in the flow stream. So as to assure that light in sufficient intensity is directed into the prism, it is preferred that the prism be positioned relatively adjacent to the arc lamp. The path of one light ray 42r may now be traced through prism assembly 45. As ray 42r exits arc lamp 40, it first encounters lens 48 whereupon it is redirected through light transmissive entry surface 61 of prism 46. Natural divergence of the light ray causes it to be reflected (by total internal reflection) at the internal walls of side surfaces 60 of the prism, as can be seen by the trace in FIG. 2. It is evident, that due to these reflections the point of exit of light ray 42r from exit surface 62 of the prism is completey uncorrelated with its point of entry into the prism. The net effect of all of the light rays within light beam 42 is illustrated in FIG. 3.

When all of the light rays of light beam 42 are reflected off the internal side walls of the prism, a homogenizing effect is produced. Thus, while it is clear that the point of exit of the light from the prism is uncorrelated with the point of entry into the prism, the homogenization of light as it travels through the prism results in a uniformly illuminated exit end of the prism. This uniform light, directed to flow chamber 22, facilitates the uniform illumination of particles 15 passing therethrough, and is particularly beneficial for uniformly exciting those particles that have been fluorescently labeled and require excitation light to actively fluoresce.

Thus, the present invention provides a straightforward technique of modifying non-uniform incoherent light to a more uniform beam of illumination directed toward flowing particles in a flow cytometry apparatus. The present invention is a significant improvement in those flow cytometry apparatuses which rely upon a source of incoherent light, such as arc lamps, for providing a source of illumination. The homogenization of light through the preferred prism of the present invention is analogous to an optical tunnel which transforms light of non-uniform magnitude, intensity and direction into a beam of illumination having substantial uniformity as it illuminates the particles to be analyzed in a flow cytometry apparatus.

What is claimed is:

1. A flow cytometry apparatus for determining characteristics of cells or the like flowing in a liquid stream comprising:

means for moving cells, substantially one at a time, in a liquid flow stream;

an excitation light source for providing a beam of incoherent light to illuminate said cells moving in said flow stream;

an elongate, solid, light transmissive prism having its longitudinal axis aligned substantially along said light beam between said source and said flow stream, said prism having internally reflective side surfaces and light transmissive end surfaces so that non-uniform incoherent light from said source directed into said prism through one of its end surfaces exits said prism through the opposite end surface in uniform fashion as the light is directed toward said cells;

means for detecting light associated with each moving cell as it passes through said area of illumination; and means for using said detected light to determine one or more characteristics of said cells.

2. The apparatus of claim 1 wherein said prism is rectangular in cross-section.

3. The apparatus of claim 1 wherein said prism is positioned in said beam of light adjacent said light source.

4. The apparatus of claim 1 wherein the cross-section of said prism is substantially constant along its longitudinal axis.

5. The apparatus of claim 4 wherein the maximum cross-sectional dimension of said prism is greater than the width of the incident beam of incoherent light adapted to enter one end surface of the prism.

6. The apparatus of claim 1 wherein the end surfaces of said prism are treated with an anti-reflectance agent to improve the efficiency of light transmission therethrough.

7. The apparatus of claim 1 which further includes a lens positioned between said light source and said prism for focusing light into the prism through said one end surface thereof.

8. The apparatus of claim 7 wherein said lens is in contact with said one end surface of said prism.

9. The apparatus of claim 8 wherein said prism and said lens are integrally formed from the same material.

10. The apparatus of claim 1 wherein said prism is made of quartz.

11. The apparatus of claim 9 wherein the integrally formed prism and lens is made of quartz.

12. The apparatus of claim 1 wherein said means for detecting light includes a device for detecting fluorescence emitted by the cells passing through said area of illumination.

13. The apparatus of claim 1 wherein said means for detecting light includes a device for detecting light scattered by the cells passing through said area of illumination.

14. A flow cytometry apparatus for determining characteristics of cells or the like flowing in a liquid stream comprising:

means for moving cells, substantially one at a time, in a liquid flow stream;

an arc lamp for providing a beam of incoherent light to illuminate said cells moving in said flow stream;

an elongate, rectangular cross-section, solid, light transmissive prism having its longitudinal axis aligned substantially along said light beam and positioned between said lamp and said flow stream, said prism having internally reflective side surfaces and light transmissive end surfaces so that non-uniform light from said lamp directed to said prism through a first end surface exists said prism through the opposite, second end surface in uniform fashion toward said cells;

a lens in contact with said first end surface of said prism and positioned adjacent to and facing said lamp for focusing light into the prism through said first end surface thereof;

means for detecting light associated with each moving cell as it passes through said area of illumination; and means for using said detected light to determine one or more characteristics of said cells.

15. The apparatus of claim 14 wherein said arc lamp is a mercury arc lamp.

16. The apparatus of claim 14 wherein the outside of said side surfaces has a protective coating thereon.

* * * * *